United States Patent [19]

Boucher et al.

[11] Patent Number: 4,501,729
[45] Date of Patent: Feb. 26, 1985

[54] AEROSOLIZED AMILORIDE TREATMENT OF RETAINED PULMONARY SECRETIONS

[75] Inventors: Richard C. Boucher; John T. Gatzy; Michael R. Knowles, all of Chapel Hill, N.C.

[73] Assignee: Research Corporation, New York, N.Y.

[21] Appl. No.: 449,424

[22] Filed: Dec. 13, 1982

[51] Int. Cl.³ .............................................. A61K 31/495
[52] U.S. Cl. ...................................... 424/45; 514/255
[58] Field of Search ................................... 424/45, 250

[56] References Cited

U.S. PATENT DOCUMENTS 4,252,809  2/1981  Knauf et al. ...................... 424/253

OTHER PUBLICATIONS

Chemical Abstracts, 93: 219063b, 1980, (Will et al.).

Primary Examiner—Leonard Schenkman
Attorney, Agent, or Firm—Scully, Scott, Murphy & Presser

[57] ABSTRACT

This disclosure describes a method of treatment of retained pulmonary secretions by the use of aerosolized suspension of amiloride.

8 Claims, No Drawings

AEROSOLIZED AMILORIDE TREATMENT OF RETAINED PULMONARY SECRETIONS

The invention described herein was made in the course of work under a grant or award made by the National Institutes of Health.

BACKGROUND OF THE INVENTION

Cystic fibrosis is a genetic disease that affects many organs and appears to reflect a generalized epithelial dysfunction. Cystic fibrosis is characterized by abnormal fluid and solute balance across the epithelia of several organs. The lung is usually the critical organ because thickened airway liquid appears to contribute to recurrent infection with progressive loss of ventilatory function. Cystic fibrosis is characterized by abnormalities that render mucus excessively thick, dehydrated and tenacious, qualities that lead to retention of material in the airways. Secretions of this nature are difficult to clear from airway surfaces and build up to obstruct airway lumens. This obstruction produces substantial impairments in respiration. Whereas the etiology of abnormal secretions is best understood in cystic fibrosis, retained secretions are important contributors to other lung diseases, e.g., asthma and chronic obstructive pulmonary disease.

The therapeutic goal in cystic fibrosis and other lung diseases is to remove retained secretions from the lung. Treatment of such pulmonary manifestations includes liquifying mucus and minimizing its formation, preventing obstruction and controlling infection. At present, only physical means (e.g., physical therapy including breathing exercises) are of any effectiveness in accomplishing this goal.

BRIEF SUMMARY OF THE INVENTION

The present invention is based upon the discovery that when an aerosolized formulation of amiloride is utilized for inhalation therapy, the drug in concentrations of $10^{-6}$–$10^{-4}$ M/L blocks removal of water from secretions. By restoring balance of water in secretions, they can be cleared. This effect cannot be achieved by amiloride via the oral route because insufficient concentrations are accumulated in airway secretions.

While we do not intend to be bound by any theory or mode of action, it appears that amiloride when administered to subjects in this manner inhibits active salt and water absorption from surface liquid and reduces the rate of water removed and hence indirectly liquifies or hydrates these secretions. These hydrated secretions are easier to transport from the lung by normal mucociliary mechanisms and cough so that the mucus obstructions are cleared from the airways and respiration is improved.

This observation has been borne out by our measurements of the transepithelial electrical potential difference across the upper and lower respiratory mucosa in patients with cystic fibrosis and control subjects. The nasal potential difference in 24 patients with cystic fibrosis exceeded by more than 3 standard deviations the mean voltage in healthy controls. Superfusion of the luminal surface with amiloride induced greater reductions in both nasal and airway potential differences in patients than in the controls. The greater reduction in potential difference in response to amiloride suggests that absorption of excess salt and liquid from respiratory epitheal surfaces contributes to the pathogenesis of lung disease in cystic fibrosis. In vitro studies of cystic fibrosis and normal respiratory epithelia confirms these inferences.

DETAILED DESCRIPTION OF THE INVENTION

In carrying out the present invention, amiloride is dissolved in a suitable vehicle such as water. The solution is nebulized in a pressure driven aerosol nebulizer or an ultrasonic nebulizer and thence applied by inhalation to the subjects. It is also within the scope of the present invention to use self-propelling amiloride suspensions for inhalation therapy by means of a non-toxic propellant, e.g., dichlorofluoromethane. Preferably the concentration of amiloride should be adequate to deposit $10^{-6}$–$10^{-4}$ M/L on the airway surfaces. An aerosol form in ranges from 3 to 10$\mu$ assures adequate aerosol deposition and retention of the drug on the airway surfaces of the lung.

The invention will be described in greater detail in conjunction with the following specific example.

EXAMPLE

A Wright pressure driven nebulizer was used to generate aerosols containing $3 \times 10^{-4}$M, $3 \times 10^{-3}$M amiloride, or vehicle (distilled water). 2.5 ml of solution was nebulized with compressed air at a flow rate of 8 L/min into a reservoir (30 L meteorologic balloon) that was connected via a Rudolph one-way valve to a cuffed and inflated endotracheal tube. Approximately 5 minutes was required to nebulize the starting material and an additional 5-7 minutes required for complete inhalation of the aerosol by the animals. For exposure to the highest amiloride concentration ($2 \times 10^{-2}$M), a DeVilbiss ultrasonic nebulizer (Model 35B) was utilized. A pediatric medication cup was employed to reduce the cannister volume so that 10 ml of solution could be nebulized and cannister cleared with a bias flow of compressed air (4 L/min) within 10 minutes. Because the flow rate with technique approximated the minute ventilation of the animals, the aerosol cannister was directly connected to a reservoir that approximated the tidal volume of a phrenic paced dog (0.5 L).

Quantitation of Aerosol Deposition and Retention: To estimate the volume of solution nebulized and deposited in the lung, a series of experiments were performed where 113 Indium DPTA (2-10 $\mu$Ci/ml) replaced amiloride in the aerosol solution. Otherwise, the preparation and both aerosol delivery systems were identical to those employed for amiloride exposure except that a catheter was inserted for sampling of venous blood. After obtaining a pre-exposure blood sample (5 ml, replaced with normal saline), aerosol exposure was initiated and serial blood samples obtained every two minutes. In some experiments, after the 10 minute aerosol exposure, pre-weighed filter paper pledgets (Whitman 541) were placed with bronchoscopy forceps on the tracheal and segmental bronchial surfaces for thirty seconds. The quantity of airway surface liquid obtained by this sampling procedure was determined by weighing the pledgets immediately after withdrawal and subtracting the pre-placement weights. The animals were immediately sacrificed with KCl or pentobarbital sodium, trachea surgically exposed, thorax opened and lungs cross-clamped at the hila. The trachea, main stem bronchi and the lungs were excised in block, blotted to gravimetrically remove blood, weighed and after addition of 250 ml of normal saline, homogenized in a blender. Blood, filter paper pledgets, aliquots of the lung homogenate (20 ml) as well as the aerosol solution (25 μl/brought to 20 ml volume) were immediately counted for radioactivity. Total aerosol deposition (μl) was calculated by dividing the sum of the counts in blood, airways and parenchyma by the specific activity of the aerolized solution. Regional concentrations in tracheal and bronchial surface liquid were expressed as μl aerosol/μl surface liquid and dilution of aerosol solution into surface liquid.

Serum Electrolytes: 5 ml venous blood samples were obtained immediately prior to and 60 minutes after aerosol exposure. Serum electrolyte concentrations were measured in a SMAC-6 (Corning). The results are reported below.

Aerosol Deposition: The sytem employing the Wright aerosol nebulizer deposited 34.0 +/− 19 μl solution (n=3) into the animal over the 10 minute exposure interval. Approximately 0.039 μl of aerosol solution/μl surface liquid was deposited on the tracheal surface and 0.013 μl/μl surface was deposited in the bronchial surface (n=2). These amounts of aerosol added to resident surface liquid would effect ~1:25 and 1:75 dilutions on tracheal and bronchial surfaces, respectively. The DeVilbiss nebulization system reproducibly deposited greater volumes of material on airway surfaces over the 10 minute exposure interval. The mean deposition was 125 +/− 7.4 μl (n=3).

Serum Electrolytes: The results from determination of serum electolytes before and one hour after exposure to aerosol were measured. No significant changes in electrolytes after amiloride exposure as compared to controls were noted.

What is claimed is:

1. A method of removing retained mucus secretions from the lungs of a subject in need of such treatment which comprises delivering an aerosol suspension of amiloride having a particle size within the range of about 3 to 10 microns to the respiratory system of said subject by inhalation of said suspension to thereby achieve concentrations on the airway surfaces of said subject of $10^{-6}M/L$–$10^{-4}M/L$ by inhibiting the reabsorption of salt and water from said secretions whereby said secretions are hydrated and are rendered easier to transport from the lung via normal mucociliary mechanisms so that the mucus obstructions are cleared from the airways and respiration is improved.

2. The method according to claim 1 in which the aerosol suspension of amiloride is generated and delivered to said subject by a pressure driven nebulizer.

3. The method according to claim 1 in which the aerosol suspension of amiloride is generated and delivered to said subject by an ultrasonic nebulizer.

4. The method according to claim 1 in which the suspension of amiloride is delivered to said subject by a non-toxic propellant.

5. A method of treating cystic fibrosis which comprises delivering an aerosol suspension of amiloride having a particle range size of about 3 to 10 microns into the lungs of a subject by inhalation of said suspension to thereby achieve concentrations on the airway surfaces of said subject of $10^{-6}M/L$–$10^{-4}M/L$ by inhibiting the reabsorption of salt and water from mucus obstructions whereby said mucus obstructions in the lungs of said subject are hydrated and are rendered easier to transport from the lungs via normal mucociliary mechanisms so that the mucus obstructions are cleared from the airways and respiration is improved.

6. The method according to claim 5 in which aerolized suspension of amiloride is generated and delivered to said subject by a pressure driven nebulizer.

7. The method according to claim 5 in which the aerolized suspension of amiloride is generated and delivered to said subject by an ultrasonic nebulizer.

8. The method according to claim 5 in which the suspension of amiloride is delivered to said subject by a non-toxic propellant.

* * * * *

UNITED STATES PATENT AND TRADEMARK OFFICE
CERTIFICATE OF CORRECTION

PATENT NO. : 4,501,729
DATED : February 26, 1985
INVENTOR(S) : Richard C. Boucher, et al.

It is certified that error appears in the above-identified patent and that said Letters Patent are hereby corrected as shown below:

After the Abstract, "8 claims" should read as --9 claims--.

Col. 2, line 67, "block" should read as --bloc--.

Col. 4, after claim 8, insert claim 9 as follows:

--9. A composition, suitable for aerosol application, contained in an ultrasonic or pressure driven nebulizer, comprising a suspension of amiloride in a pharmaceutical carrier, the amiloride having a particle size range of about 3 to 10 microns and being present in a sufficient amount to provide concentrations upon application thereof on respiratory epithelial airway surfaces of a subject of from $10^{-6}$ M/L-$10^{-4}$ M/L.--

Signed and Sealed this

Twenty-third Day of July 1985

[SEAL]

Attest:

DONALD J. QUIGG

Attesting Officer

Acting Commissioner of Patents and Trademarks